(12) United States Patent
Pan et al.

(10) Patent No.: US 11,491,134 B2
(45) Date of Patent: Nov. 8, 2022

(54) COMPOSITION FOR INHIBITING SKIN CELL PROLIFERATION AND/OR ANTI-INFLAMMATION METHOD FOR INHIBITING SKIN CELL PROLIFERATION AND/OR ANTI-INFLAMMATION AND METHOD FOR TREATING SKIN DISEASES AND/OR INFLAMMATORY DISEASES

(71) Applicant: Industrial Technology Research Institute, Hsinchu (TW)

(72) Inventors: I-Hong Pan, Zhubei (TW); Ming-Han Li, Hsinchu (TW); Kai-An Chuang, Taoyuan (TW); Shu-Fang Wen, Baoshan Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 77 days.

(21) Appl. No.: 16/731,658

(22) Filed: Dec. 31, 2019

(65) Prior Publication Data
US 2020/0397745 A1 Dec. 24, 2020

Related U.S. Application Data

(60) Provisional application No. 62/864,129, filed on Jun. 20, 2019.

(51) Int. Cl.
*A61K 31/353* (2006.01)
*A61K 9/00* (2006.01)
*A61P 17/06* (2006.01)
*A61P 29/00* (2006.01)
*A61K 9/06* (2006.01)

(52) U.S. Cl.
CPC .......... *A61K 31/353* (2013.01); *A61K 9/0014* (2013.01); *A61K 9/06* (2013.01); *A61P 17/06* (2018.01); *A61P 29/00* (2018.01)

(58) Field of Classification Search
CPC ...... A61K 31/353; A61K 9/0014; A61K 9/06; A61K 47/20; A61P 17/06; A61P 29/00
USPC .......................................................... 514/456
See application file for complete search history.

(56) References Cited

U.S. PATENT DOCUMENTS

| | | | |
|---|---|---|---|
| 7,998,971 B2 | 8/2011 | Barlow et al. | |
| 8,557,306 B2 | 10/2013 | Tripp et al. | |
| 9,669,062 B2 | 6/2017 | Shraibom | |
| 10,226,499 B2 | 3/2019 | Rozenblat et al. | |
| 2010/0184857 A1 | 7/2010 | Babish et al. | |

FOREIGN PATENT DOCUMENTS

| | | |
|---|---|---|
| CN | 102302483 A | 1/2012 |
| CN | 102349959 A | 2/2012 |
| CN | 102711743 A | 10/2012 |
| CN | 104109145 A | 10/2014 |
| CN | 106236808 A | 12/2016 |
| CN | 106333994 A | 1/2017 |
| TW | 200930389 A | 9/1997 |

OTHER PUBLICATIONS

Attrarde et al , Validation and Development of HPTLC Method for Simultaneous Estimation of Apigenin and Luteolin in Selected Marketed Ayurvedic Formulations of 'Dashmula' and in Ethyl Acetate Extract of Premna integrifolia L, J. Anal. Bioanal. Tech., 2017, vol. 8, issue 1, p. 1-9. (Year: 2017).*
Rowe et al , Handbook of Pharmaceutical Excipients, Sixth ed. 2009, Ethyl Acetate, , p. 253-255. (Year: 2009).*
Chinese Office Action for Appl. No. 202010342661.8 dated May 8, 2021.
Cho, B.O. et al., "Synergistic Anti-inflammatory Effect of Rosmarinic Acid and Luteolin in Lipopolysaccharide-Stimulated RAW264.7 Macrophage Cells," Korean Journal of Food Science and Technology, 2015, vol. 47, No. 1, pp. 119-125.
Sun, Y.S., et al., "Inhibition of apigenin on lipopolysaccharide-induced bone-marrow-derived macrophages inflammation through NF-KB and MAPK", Journal of Food Safety and Quality, 2017, vol. 8, No. 3, pp. 942-947.
Wang, S., et al., "Effect of luteolin on inflammatory responses in RAW264.7 macrophages activated with LPS and IFN-γ," Journal of Functional Foods, 2017, vol. 32, pp. 123-130.
Weng, Z., et al., "Luteolin Inhibits Human Keratinocyte Activation and Decreases NF-KB Induction That Is Increased in Psoriatic Skin", Plos One, 2014, vol. 9, pp. 1-7.
Wu, G., et al., "Molecular mechanism of apigenin on inhibition of LPS-induced inflammatory mediators in murine macrophages," Cellular & Molecular Immunology, 2015, pp. 753-757.
Ali et al., "Health functionality of apigenin: A review", International Journal of Food Properties, 2017 (published online Dec. 18, 2016), vol. 20, No. 6, 1197-1238 (43 pages).
Imran et al., "Luteolin, a flavonoid, as an anticancer agent: a review", Biomedicine & Pharmacotherapy, 2019, vol. 112, pp. 1-10.
Taiwanese Office Action and Search Report, dated Sep. 26, 2020, for Taiwanese Application No. 108148607.
Balasubramanian et al., "Apigenin Inhibition of Involucrin Gene Expression is Associated with a Specific Reduction in Phosphorylation of Protein Kinase Cσ Tyr $^{311}$", The Journal of Biological Chemistry, Nov. 24, 2006, vol. 281, No. 47, pp. 36162-36172(12 pages).
Balasubramanian et al., "Keratinocyte proliferation, differentiation, and apoptosis—Differential mechanisms of regulation by curcumin, EGCG and apigenin", Toxicology and Applied Pharmacology, 2007 (available online Mar. 30, 2007), vol. 224, pp. 214-219 (6 pages).
Chou, "Drug Combination Studies and Their Synergy Quantification Using the Chou-Talalay Method", Cancer Res, Jan. 15, 2010, vol. 70, No. 2, pp. 440-446 (8 pages).

(Continued)

*Primary Examiner* — Taylor V Oh

(74) *Attorney, Agent, or Firm* — Birch, Stewart, Kolasch & Birch, LLP

(57) ABSTRACT

A composition for inhibiting skin cell proliferation and/or anti-inflammation is provided. The composition for inhibiting skin cell proliferation and/or anti-inflammation includes: apigenin and luteolin, wherein a weight ratio of the apigenin to the luteolin is about 1.5-25:1, or a mole ratio of the apigenin to the luteolin is about 1.5-25:1. Moreover, the apigenin and the luteolin have a synergistic effect on inhibiting skin cell proliferation and/or anti-inflammation.

9 Claims, No Drawings

(56) References Cited

OTHER PUBLICATIONS

George et al., "Comparative Studies to Evaluate Relative in vitro Potency of Luteolin in Inducing Cell Cycle Arrest and Apoptosis in HaCaT and A375 Cells", Asian Pacific J Cancer Prev, 2013, vol. 14, No. 2, pp. 631-637 (7 pages).

Hayasaka et al., "Absorption and Metabolism of Luteolin in Rats and Humans in Relation to in Vitro Anti-inflammatory Effects", J. Agric. Food Chem., 2018, vol. 66, pp. 11320-11329 (18 pages).

Lee et al., "Resveratrol as a Bioenhancer to Improve Anti-Inflammatory Activities of Apigenin", Nutrients, 2015, vol. 7, pp. 9650-9661 (12 pages).

Palombo et al., "Luteolin-7-glucoside inhibits IL-22/STAT3 pathway, reducing proliferation, acanthosis, and inflammation in keratinocytes and in mouse psoriatic model", Cell and Death and Disease, 2016, vol. 7, pp. 1-11 (11 pages).

Rakariyatham et al., "Synergism between luteolin and sulforaphane in ant-inflammation", Food Funct., Oct. 2018, vol. 9, pp. 5115-5123 (18 pages).

Sung et al., "Anti-Inflammatory Activity of Butein and Luteolin Through Suppression of NFkB Activation and Induction of Heme Oxygenase-1", Journal of Medicinal Food, 2015, vol. 00, No. 0, pp. 1-8 (8 pages).

Weng et al., "Luteolin Inhibits Human Keratinocyte Activation and Decreases NF-kB Induction That is Increased in Psoriatic Skin", Plos One, Feb. 2014, vol. 9, No. 2, pp. 1-8 (8 pages).

Zhang et al., "Flavonoid Apigenin Inhibits Lipopolysaccharide-Induced Inflammatory Response through Multiple Mechanisms in Macrophages", PloS One, Sep. 2014, vol. 9, No. 9, pp. 1-18 (18 pages).

Office Action issued in Chinese Patent Application No. 202010342661.8 dated Dec. 27, 2021.

* cited by examiner

COMPOSITION FOR INHIBITING SKIN CELL PROLIFERATION AND/OR ANTI-INFLAMMATION METHOD FOR INHIBITING SKIN CELL PROLIFERATION AND/OR ANTI-INFLAMMATION AND METHOD FOR TREATING SKIN DISEASES AND/OR INFLAMMATORY DISEASES

CROSS REFERENCE TO RELATED APPLICATION

This application claims the benefit of U.S. Provisional Application No. 62/864,129, filed on Jun. 20, 2019, the entirety of which is incorporated by reference herein.

TECHNICAL FIELD

The present disclosure is related to a synergistic composition comprising apigenin and luteolin, and is particularly related to a composition for inhibiting skin cell proliferation and/or anti-inflammation comprising apigenin and luteolin, and a use of apigenin and luteolin in the preparation a composition for inhibiting skin cell proliferation and/or anti-inflammation.

BACKGROUND

Skin diseases are the most common disease in the world, and in terms of health care spending, skin-related medical costs can reach as high as 25%.

Skin diseases can be divided into four major categories, namely dermatitis (such as allergic and contact), cancer (such as melanoma), immune disease (such as psoriasis), and infectious skin disease (such as bacterial, fungal, and viral infections).

At present, there is literature that points to flavonoids such as apigenin and luteolin having cell proliferation inhibition and anti-inflammatory activity, but the interaction between the two remains unclear.

Therefore, it is currently expected that synergistic compositions containing apigenin and luteolin can be obtained to provide drugs which have better efficacy but can be used at lower doses, and can be applied to the treatment of skin diseases or inflammatory diseases.

SUMMARY

The present disclosure provides a composition for inhibiting skin cell proliferation and/or anti-inflammation, comprising: apigenin; and luteolin, wherein a weight ratio of the apigenin to the luteolin is about 1.5-25:1 or a mole ratio of the apigenin to the luteolin is about 1.5-25:1. Moreover, the apigenin and the luteolin have a synergistic effect on inhibiting skin cell proliferation and/or anti-inflammation.

The present disclosure further provides a use of apigenin and luteolin in the preparation a composition for inhibiting skin cell proliferation and/or anti-inflammation, wherein a weight ratio of the apigenin to the luteolin is about 1.5-25:1 or a mole ratio of the apigenin to the luteolin is about 1.5-25:1. Moreover, the apigenin and the luteolin have a synergistic effect on inhibiting skin cell proliferation and/or anti-inflammation.

The present disclosure may also provide a method for inhibiting skin cell proliferation and/or anti-inflammation, comprising administering the foregoing composition for inhibiting skin cell proliferation and/or anti-inflammation to a subject in need thereof.

The present disclosure may also provide a method for treating skin diseases and/or inflammatory diseases, comprising administering the foregoing composition for inhibiting skin cell proliferation and/or anti-inflammation to a subject in need thereof.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

The present disclosure may provide a composition for inhibiting skin cell proliferation and/or anti-inflammation which may be a synergistic composition that comprises, but is not limited to, apigenin and luteolin.

In the foregoing composition for inhibiting skin cell proliferation and/or anti-inflammation of the present disclosure, the apigenin and the luteolin may have a synergistic effect on inhibiting skin cell proliferation, anti-inflammation, etc., or any combination of thereof, but it is not limited thereto.

"Having a synergistic effect" mentioned in the present disclosure may mean that, for a specific physiological or medical purpose, a plurality of ingredients are analyzed for their combination by CalcuSyn software, and the combination thereof is confirmed that the combination index (CI) is less than 1 (Ting-Chao Chou; Cancer Res; 70 (2) Jan. 15, 2010), or may mean that when the total content or concentration used is the same, compared to a plurality of ingredients which are present separately, the combination of the plurality of ingredients has better efficacy for a specific physiological or medical purpose, but the meaning is not limited thereto.

In one embodiment, in the foregoing composition for inhibiting skin cell proliferation and/or anti-inflammation of the present disclosure, whether the apigenin and the luteolin have a synergistic effect on inhibiting skin cell proliferation and/or anti-inflammation, is evaluated by the combination index of the combination of apigenin and luteolin.

Furthermore, examples of a skin cell may comprise, but are not limited to, a keratinocyte and a skin fibroblast. In addition, the foregoing inflammation may comprise, but is not limited to, an inflammatory response involving immune cells, such as macrophages.

In the foregoing composition for inhibiting skin cell proliferation and/or anti-inflammation of the present disclosure, a weight ratio of the apigenin to the luteolin may be about 1.5-25:1, such as about 1.5-20:1, about 1.5-15:1, about 1.5-12:1, about 1.5-10:1, about 2-25:1, about 2-20:1, about 2-15:1, about 2-12:1, about 2-10:1, about 1.5:1, about 1.9:1, about 2:1, about 3:1, about 4:1, about 4.7:1, about 5:1, about 9:1, about 9.4:1, about 10:1, about 12:1, about 15:1, about 18.8:1, about 19:1, about 20:1, about 25:1. Alternatively, in the foregoing composition for inhibiting skin cell proliferation and/or anti-inflammation of the present disclosure, a mole ratio of the apigenin to the luteolin may be about 1.5-25:1, such as about 1.5-20:1, about 1.5-15:1, about 1.5-12:1, about 1.5-10:1, about 2-25:1, about 2-20:1, about 2-15:1, about 2-12:1, about 2-10:1, about 1.5:1, about 2:1, about 3:1, about 4:1, about 5:1, about 10:1, about 12:1, about 15:1, about 20:1, about 25:1, but it is not limited thereto.

In one embodiment, in the foregoing composition for inhibiting skin cell proliferation and/or anti-inflammation of the present disclosure, the apigenin and the luteolin may have a synergistic effect on inhibiting skin cell proliferation. In this embodiment, in the foregoing composition for inhibiting skin cell proliferation and/or anti-inflammation of the present disclosure, the weight ratio of the apigenin to the luteolin may be about 1.5-15:1, such as about 1.5-12:1, about 1.5-10:1, about 2-15:1, about 2-12:1, about 2-10:1, about 1.5:1, about 1.9:1, about 2:1, about 3:1, about 4:1, about 4.7:1, about 5:1, about 9:1, about 9.4:1, about 10:1, about 12:1, about 15:1. Alternatively, in the foregoing composition for inhibiting skin cell proliferation and/or anti-inflammation of the present disclosure, the mole ratio of the apigenin to the luteolin may be about 1.5-15:1, such as about 1.5-12:1, about 1.5-10:1, about 2-15:1, about 2-12:1, about 2-10:1, about 1.5:1, about 2:1, about 3:1, about 4:1, about 5:1, about 10:1, about 12:1, about 15:1, but it is not limited thereto.

In another embodiment, in the foregoing composition for inhibiting skin cell proliferation and/or anti-inflammation of the present disclosure, the apigenin and the luteolin may have a synergistic effect on anti-inflammation. In this embodiment, in the foregoing composition for inhibiting skin cell proliferation and/or anti-inflammation of the present disclosure, the weight ratio of the apigenin to the luteolin may be about 1.5-25:1, such as about 1.5-20:1, about 1.5-15:1, about 1.5-12:1, about 1.5-10:1, about 2-25:1, about 2-20:1, about 2-15:1, about 2-12:1, about 2-10:1, about 1.5:1, about 1.9:1, about 2:1, about 3:1, about 4:1, about 4.7:1, about 5:1, about 9:1, about 9.4:1, about 10:1, about 12:1, about 15:1, about 18.8:1, about 19:1, about 20:1, about 25:1. Alternatively, in the foregoing composition for inhibiting skin cell proliferation and/or anti-inflammation of the present disclosure, the mole ratio of the apigenin to the luteolin may be about 1.5-25:1, such as about 1.5-20:1, about 1.5-15:1, about 1.5-12:1, about 1.5-10:1, about 2-25:1, about 2-20:1, about 2-15:1, about 2-12:1, about 2-10:1, about 1.5:1, about 2:1, about 3:1, about 4:1, about 5:1, about 10:1, about 12:1, about 15:1, about 20:1, about 25:1, but it is not limited thereto.

In yet another embodiment, in the foregoing composition for inhibiting skin cell proliferation and/or anti-inflammation of the present disclosure, the apigenin and the luteolin may have a synergistic effect on both of inhibiting skin cell proliferation and anti-inflammation. In this embodiment, in the foregoing composition for inhibiting skin cell proliferation and/or anti-inflammation of the present disclosure, the weight ratio of the apigenin to the luteolin may be about 1.5-15:1, such as about 1.5-12:1, about 1.5-10:1, about 2-15:1, about 2-12:1, about 2-10:1, about 1.5:1, about 1.9:1, about 2:1, about 3:1, about 4:1, about 4.7:1, about 5:1, about 9:1, about 9.4:1, about 10:1, about 12:1, about 15:1. Alternatively, in the foregoing composition for inhibiting skin cell proliferation and/or anti-inflammation of the present disclosure, the mole ratio of the apigenin to the luteolin may be about 1.5-15:1, such as about 1.5-12:1, about 1.5-10:1, about 2-15:1, about 2-12:1, about 2-10:1, about 1.5:1, about 2:1, about 3:1, about 4:1, about 5:1, about 10:1, about 12:1, about 15:1, but it is not limited thereto.

In one embodiment, the foregoing composition for inhibiting skin cell proliferation and/or anti-inflammation of the present disclosure, in addition to the apigenin and the luteolin, may further comprise a pharmaceutically acceptable vehicle, carrier or salt, but it is not limited thereto. In this embodiment, in the foregoing composition for inhibiting skin cell proliferation and/or anti-inflammation of the present disclosure, a total content of the apigenin and the luteolin may be about 0.1-20 wt %, such as 0.2-15 wt %, 0.3-10 wt %, 0.5 wt %, 1 wt %, 1.5 wt %, 2 wt %, 2.5 wt %, 3 wt %, 4 wt %, 5 wt %, but it is not limited thereto.

The pharmaceutically acceptable vehicles may act as a dilutant, dispersant or carrier for the active ingredient. The pharmaceutically acceptable vehicle may comprise materials commonly employed in skin care products such as water, liquid or solid emollients, silicone oils, emulsifiers, solvents, humectants, thickeners, powders, propellants and the like.

The vehicle may be formed from 80%-99.9 wt %, for example, 95-99.5% by weight of the compositions mentioned above, and can, in the absence of other adjuncts, form the balance of the compositions.

In addition, in one embodiment, all of the compositions mentioned above may be prepared as a skin spreading form, including, but not limited to creams, ointments, gels, sprays, lotions, skin tonics, shampoos or mousses, etc. Skin sprays are generally composed of aerosolized copolymers, such as polyvinylpyrrolidone, vinyl acetate and the like, and may also function as a setting lotion. Skin gel preparations are similar to sprays in composition, but are in gel and alcohol free form, and can coat the skin. A skin mousse is foam released under pressure from an aerosolized can. Skin creams may be a hydrophobic or hydrophilic cream, ointment, gel, emollient, spray, lotion, skin tonic, shampoo or mousse. Furthermore, suitable ingredients may be further added to the skin cream, and such additionally added ingredients can include petrolatum, waxes, lanolin, silicone, liposomes, vegetable, mineral oils, plasticizers, fragrances, preservatives, a penetration enhancing agent, a pH adjusting agent or other suitable ingredients for skin creams. Such additional ingredients can moisturize skin, stabilize the active compound, increase the composition-skin contact to further raise local concentration and control the composition release.

Moreover, other specific ingredients which benefit skin, such as sunscreens and skin-lightening agents may be also included in the compositions mentioned above. The vehicle may also further include adjuncts such as antioxidants, perfumes, opacifiers, preservatives, colorants and buffers.

The pharmaceutically acceptable carrier mentioned above may comprise, but is not limited to, a solvent, a dispersion medium, a coating, an antibacterial and antifungal agent, or an isotonic and absorption delaying agent, etc. which is suitable for pharmaceutical administration. The pharmaceutical composition can be formulated into dosage forms for different administration routes utilizing conventional methods.

Furthermore, the pharmaceutically acceptable salt mentioned above may include, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

Example of the forgoing composition for inhibiting skin cell proliferation and/or anti-inflammation of the present disclosure may comprise, but is not limited to, a pharmaceutical composition or a health care composition.

The pharmaceutical composition or health care composition of the present disclosure may be administered orally, parenterally by an inhalation spray, or via an implanted reservoir. The parenteral methods may comprise smearing any region in skin or a region with demand in skin, subcutaneous, intracutaneous, intravenous, intramuscular, intra-articular, intra-arterial, intrasynovial, intrasternal, intrathecal, and intraleaional injection, as well as infusion techniques.

An oral composition may include, but is not limited to, tablets, capsules, emulsions, and aqueous suspensions, dispersions and solutions.

Topically used form for smearing may comprise ointments, creams, solutions, gels, etc. but they are not limited thereto.

In one specific embodiment, the composition for inhibiting skin cell proliferation and/or anti-inflammation of the present disclosure mentioned above may be a pharmaceutical composition. In this specific embodiment, the pharmaceutical composition may be a topical dosage form, wherein the topical dosage form may include ointments, creams, solutions or gels, etc., but it is not limited thereto. Moreover, in this specific embodiment, the pharmaceutical composition may comprise, but is not limited to, a pharmaceutical composition for treating skin diseases and/or inflammatory diseases. In addition, example of the pharmaceutical composition for treating skin diseases and/or inflammatory diseases mentioned above may comprise, but is not limited to, a pharmaceutical composition for treating psoriasis, a pharmaceutical composition for treating allergic or contact dermatitis, etc.

Based on the foregoing, the present disclosure may further provide a use of apigenin and luteolin in the preparation a composition for inhibiting skin cell proliferation and/or anti-inflammation. In the use of apigenin and luteolin in the preparation a composition for inhibiting skin cell proliferation and/or anti-inflammation of the present disclosure, the apigenin and the luteolin have a synergistic effect on inhibiting skin cell proliferation and/or anti-inflammation.

Furthermore, all relevant interpretations for the apigenin and the luteolin which are involved in the use of apigenin and luteolin in the preparation a composition for inhibiting skin cell proliferation and/or anti-inflammation of the present disclosure can be referred to the relevant descriptions for the apigenin and the luteolin in the preceding paragraphs describing the composition for inhibiting skin cell proliferation and/or anti-inflammation of the present disclosure, and thus they are not repeated herein.

In one embodiment, in the use of apigenin and luteolin in the preparation a composition for inhibiting skin cell proliferation and/or anti-inflammation of the present disclosure, a pharmaceutically acceptable vehicle, carrier or salt can also be used in the preparation of the composition for inhibiting skin cell proliferation and/or anti-inflammation.

Moreover, the relevant interpretations for the pharmaceutically acceptable vehicle, carrier or salt can be referred to the relevant descriptions in the preceding paragraphs describing the composition for inhibiting skin cell proliferation and/or anti-inflammation of the present disclosure, and thus they are not repeated herein.

In addition, all relevant interpretations for the composition for inhibiting skin cell proliferation and/or anti-inflammation prepared in the use of apigenin and luteolin in the preparation a composition for inhibiting skin cell proliferation and/or anti-inflammation of the present disclosure mentioned above can be referred to all relevant descriptions in the preceding paragraphs describing the composition for inhibiting skin cell proliferation and/or anti-inflammation of the present disclosure, but it is not limited thereto.

Furthermore, according to the foregoing, the present disclosure may further provide a method for inhibiting skin cell proliferation and/or anti-inflammation. The method mentioned above may comprise, but is not limited to, administering the any composition for inhibiting skin cell proliferation and/or anti-inflammation of the present disclosure mentioned above to a subject in need thereof.

Furthermore, according to the foregoing, the present disclosure may also provide a method for treating skin diseases and/or inflammatory diseases. The method mentioned above may comprise, but is not limited to, administering the any composition for inhibiting skin cell proliferation and/or anti-inflammation of the present disclosure mentioned above to a subject in need thereof.

The skin disease mentioned herein may comprise, but is not limited to, psoriasis or allergic or contact dermatitis, etc.

The subject mentioned in the present disclosure may comprise, but is not limited to, a vertebrate. The vertebrate mentioned above may comprise a fish, an amphibian, a reptile, a bird or a mammal, but it is not limited thereto. Examples of the mammal may comprise, but are not limited to a human, an orangutan, a monkey, a horse, a donkey, a dog, a cat, a rabbit, a guinea pig, a rat and a mouse. In one embodiment, the said subject may be a human.

Furthermore, the administration manners for the composition in the all treatment methods of the present disclosure can be referred to the relevant descriptions in the preceding paragraphs describing the composition for inhibiting skin cell proliferation and/or anti-inflammation of the present disclosure, and thus they are not repeated herein.

EXAMPLES

1. Determination of Inhibition Rate on Keratinocyte (HaCaT Cell) Proliferation

1-1. Methods

Dimethyl sulfoxide (DMSO) was used as a solvent to prepare apigenin test samples with different concentrations and luteolin test samples with different concentrations. 9 batches of experiments were performed, which respectively were Batch 1 to Batch 9. There were 6 independent experiments in each batch of experiments.

In each independent experiment, inhibition rate of an apigenin test sample with a specific concentration on keratinocyte proliferation and inhibition rate of a luteolin test sample with a specific concentration on keratinocyte proliferation were determined, and inhibition rate of a combination of an apigenin test sample with the said specific concentration and a luteolin test sample with the said specific concentration on keratinocyte proliferation was determined. Between the independent experiments, concentrations of apigenin test samples used were different, and concentrations of luteolin test samples used were also different, however, mole ratios or weight ratios of apigenin test samples to luteolin test samples were the same.

Moreover, between the batches of experiments, mole ratios or weight ratios of apigenin test samples to luteolin test samples were different.

The experimental operation is described as follows:

$5 \times 10^3$ keratinocytes, HaCaT cells, were inoculated in a 96-well culture plate and then placed in a 37° C. and 5% $CO_2$ incubator for culturing overnight, and cell numbers at this time point (T0) was used as a benchmark for cell proliferation.

After overnight culture, a test sample was added to the cells in the culture plate (refer to Table 1, and the cells of the control group were only treated with dimethyl sulfoxide) for co-culturing for 48 hours (T48). After that, the supernatant in the culture plate was removed.

After the supernatant was removed, 50 μL MTT solution (0.5 mg/mL; Life Technologies Cat. No. M-6494) was added to cells and then the culture plate was placed in a 37° C. and 5% $CO_2$ incubator for culturing for 1.5 hours. After that, 150 μL DMSO (J. T. Baker, Cat. No. 9224-03) was added to the cells in the culture plate and shaken for 5 minutes.

Thereafter, the absorbance of each well of the culture plate was determined at 570 nm by a continuous wavelength microplate reader, and inhibition rate on cell proliferation was calculated through the following formula:

Inhibition rate on cell proliferation=$T$48 Control group$_{570\ nm}$−$T$48 Experimental group$_{570\ nm}$)/ ($T$48 Control group$_{570\ nm}$−$T$0 Control group$_{570\ nm}$)

1-2. Results

Inhibition rate of each test sample on cell proliferation is shown in the following Table 1.

TABLE 1

| Apigenin (μM)/ Apigenin (μg/mL) | Inhibition rate | Luteolin (μM)/ Luteolin (μg/mL) | Inhibition rate | Apigenin (μM) + Luteolin (μM) | Inhibition rate |
|---|---|---|---|---|---|
| \multicolumn{6}{c}{Batch 1: Mole ratio of apigenin to luteolin = 1:1 or weight ratio of apigenin to luteolin = about 0.94:1} | | | | | |
| 100/27.02 | 1.032 | 100/28.62 | 1.009 | 100 + 100 | 1.087 |
| 50/13.51 | 0.722 | 50/14.31 | 0.677 | 50 + 50 | 0.982 |
| 25/6.76 | 0.292 | 25/7.16 | 0.446 | 25 + 25 | 0.578 |
| 12.5/3.38 | 0.122 | 12.5/3.58 | 0.172 | 12.5 + 12.5 | 0.238 |
| 6.25/1.69 | 0.000 | 6.25/1.79 | 0.009 | 6.25 + 6.25 | 0.029 |
| 3.125/0.84 | 0.000 | 3.125/0.89 | 0.000 | 3.125 + 3.125 | 0.000 |
| Batch 2: Mole ratio of apigenin to luteolin = 2:1 or weight ratio of apigenin to luteolin = about 1.9:1 | | | | | |
| 100/27.02 | 1.051 | 50/14.31 | 0.752 | 100 + 50 | 1.087 |
| 50/13.51 | 0.756 | 25/7.16 | 0.538 | 50 + 25 | 0.946 |
| 25/6.76 | 0.407 | 12.5/3.58 | 0.350 | 25 + 12.5 | 0.520 |
| 12.5/3.38 | 0.157 | 6.25/1.79 | 0.196 | 12.5 + 6.25 | 0.298 |
| 6.25/1.69 | 0.058 | 3.125/0.89 | 0.051 | 6.25 + 3.125 | 0.156 |
| 3.125/0.84 | 0.037 | 1.5625/0.45 | 0.113 | 3.125 + 1.5625 | 0.129 |
| Batch 3: Mole ratio of apigenin to luteolin = 5:1 or weight ratio of apigenin to luteolin = about 4.7:1 | | | | | |
| 100/27.02 | 1.031 | 20/5.72 | 0.556 | 100 + 20 | 1.049 |
| 50/13.51 | 0.753 | 10/2.86 | 0.319 | 50 + 10 | 0.799 |
| 25/6.76 | 0.397 | 5/1.43 | 0.137 | 25 + 5 | 0.400 |
| 12.5/3.38 | 0.172 | 2.5/0.72 | 0.043 | 12.5 + 2.5 | 0.187 |
| 6.25/1.69 | 0.050 | 1.25/0.36 | 0.028 | 6.25 + 1.25 | 0.099 |
| 3.125/0.84 | 0.000 | 0.625/0.18 | 0.019 | 3.125 + 0.625 | 0.023 |
| Batch 4: Mole ratio of apigenin to luteolin = 10:1 or weight ratio of apigenin to luteolin = about 9.4:1 | | | | | |
| 100/27.02 | 1.035 | 10/2.86 | 0.066 | 100 + 10 | 1.043 |
| 50/13.51 | 0.719 | 5/1.43 | 0.008 | 50 + 5 | 0.801 |
| 25/6.76 | 0.319 | 2.5/0.72 | 0.000 | 25 + 2.5 | 0.315 |
| 12.5/3.38 | 0.089 | 1.25/0.36 | 0.000 | 12.5 + 1.25 | 0.106 |
| 6.25/1.69 | 0.000 | 0.625/0.18 | 0.000 | 6.25 + 0.625 | 0.000 |
| 3.125/0.84 | 0.000 | 0.3125/0.09 | 0.004 | 3.125 + 0.3125 | 0.000 |
| Batch 5: Mole ratio of apigenin to luteolin = 20:1 or weight ratio of apigenin to luteolin = about 18.8:1 | | | | | |
| 100/27.02 | 1.103 | 5/1.43 | 0.033 | 100 + 5 | 1.069 |
| 50/13.51 | 0.771 | 2.5/0.72 | 0.000 | 50 + 2.5 | 0.761 |
| 25/6.76 | 0.362 | 1.25/0.36 | 0.000 | 25 + 1.25 | 0.326 |
| 12.5/3.38 | 0.183 | 0.625/0.18 | 0.043 | 12.5 + 0.625 | 0.162 |
| 6.25/1.69 | 0.111 | 0.3125/0.09 | 0.140 | 6.25 + 0.3125 | 0.016 |
| 3.125/0.84 | 0.023 | 0.15625/0.04 | 0.114 | 3.125 + 0.15625 | 0.000 |
| Batch 6: Mole ratio of apigenin to luteolin = 1:2 or weight ratio of apigenin to luteolin = about 1:2.1 | | | | | |
| 50/13.51 | 0.720 | 100/28.62 | 0.942 | 50 + 100 | 0.986 |
| 25/6.76 | 0.487 | 50/14.31 | 0.578 | 25 + 50 | 0.737 |
| 12.5/3.38 | 0.013 | 25/7.16 | 0.422 | 12.5 + 25 | 0.388 |
| 6.25/1.69 | 0.000 | 12.5/3.58 | 0.185 | 6.25 + 12.5 | 0.172 |
| 3.125/0.84 | 0.000 | 6.25/1.79 | 0.006 | 3.125 + 6.25 | 0.000 |
| 1.5625/0.42 | 0.000 | 3.125/0.89 | 0.000 | 1.5625 + 3.125 | 0.000 |
| Batch 7: Mole ratio of apigenin to luteolin = 1:5 or weight ratio of apigenin to luteolin = about 1:5.3 | | | | | |
| 20/5.40 | 0.404 | 100/28.62 | 1.078 | 20 + 100 | 1.118 |
| 10/2.70 | 0.247 | 50/14.31 | 0.701 | 10 + 50 | 0.717 |
| 5/1.35 | 0.087 | 25/7.16 | 0.551 | 5 + 25 | 0.546 |
| 2.5/0.68 | 0.128 | 12.5/3.58 | 0.375 | 2.5 + 12.5 | 0.329 |
| 1.25/0.34 | 0.083 | 6.25/1.79 | 0.190 | 1.25 + 6.25 | 0.106 |
| 0.625/0.17 | 0.080 | 3.125/0.89 | 0.086 | 0.625 + 3.125 | 0.039 |

TABLE 1-continued

Inhibition rate of each test sample on cell proliferation

| Apigenin (μM)/ Apigenin (μg/mL) | Inhibition rate | Luteolin (μM)/ Luteolin (μg/mL) | Inhibition rate | Apigenin (μM) + Luteolin (μM) | Inhibition rate |
|---|---|---|---|---|---|
| Batch 8: Mole ratio of apigenin to luteolin = 1:10 or weight ratio of apigenin to luteolin = about 1:10.6 | | | | | |
| 10/2.70 | 0.183 | 100/28.62 | 1.000 | 10 + 100 | 1.008 |
| 5/1.35 | 0.104 | 50/14.31 | 0.636 | 5 + 50 | 0.649 |
| 2.5/0.68 | 0.089 | 25/7.16 | 0.507 | 2.5 + 25 | 0.512 |
| 1.25/0.34 | 0.101 | 12.5/3.58 | 0.335 | 1.25 + 12.5 | 0.327 |
| 0.625/0.17 | 0.090 | 6.25/1.79 | 0.138 | 0.625 + 6.25 | 0.133 |
| 0.3125/0.08 | 0.043 | 3.125/0.89 | 0.052 | 0.3125 + 3.125 | 0.036 |
| Batch 9: Mole ratio of apigenin to luteolin = 1:20 or weight ratio of apigenin to luteolin = about 1:21 | | | | | |
| 5/1.35 | 0.032 | 100/28.62 | 1.037 | 5 + 100 | 0.987 |
| 2.5/0.68 | 0.032 | 50/14.31 | 0.620 | 2.5 + 50 | 0.601 |
| 1.25/0.34 | 0.046 | 25/7.16 | 0.478 | 1.25 + 25 | 0.456 |
| 0.625/0.17 | 0.021 | 12.5/3.58 | 0.301 | 0.625 + 12.5 | 0.263 |
| 0.3125/0.08 | 0.039 | 6.25/1.79 | 0.110 | 0.3125 + 6.25 | 0.068 |
| 0.15625/0.04 | 0.014 | 3.125/0.89 | 0.042 | 0.15625 + 3.125 | 0.031 |

2. Determination of Inhibition Rate on Inflammation (Anti-Inflammatory Activity)

2-1. Methods

Dimethyl sulfoxide (DMSO) was used as a solvent to prepare apigenin test samples with different concentrations and luteolin test samples with different concentrations. 9 batches of experiments were performed, which respectively were Batch 1 to Batch 9. There were 6 independent experiments in each batch of experiments.

In each independent experiment, inhibition rate of an apigenin test sample with a specific concentration on inflammation and inhibition rate of a luteolin test sample with a specific concentration on inflammation were determined, and inhibition rate of a combination of an apigenin test sample with the said specific concentration and a luteolin test sample with the said specific concentration on inflammation was determined. Between the independent experiments, concentrations of apigenin test samples used were different, and concentrations of luteolin test samples used were also different, however, mole ratios or weight ratios of apigenin test samples to luteolin test samples were the same.

Moreover, between the batches of experiments, mole ratios or weight ratios of apigenin test samples to luteolin test samples were different.

$5 \times 10^4$ macrophages, RAW264.7 cells, were inoculated in a 96-well culture plate and then placed in a 37° C. and 5% $CO_2$ incubator for culturing overnight.

After overnight culture, the supernatant was removed, and lipopolysaccharide (LPS) (50 ng/mL) and a test sample was added to the cells (refer to Table 2, and the cells of the induced group were treated with lipopolysaccharide and dimethyl sulfoxide while the cells of the control group were only treated with dimethyl sulfoxide) for reaction for 24 hours.

Thereafter, the supernatant of each well in the culture plate was transferred to a new culture plate and reacted with Griess reagent (Promega, Cat. No. G2930), respectively, and then the absorbance of each well of the culture plate was determined at 540 nm by a continuous wavelength microplate reader to evaluate the content of nitric oxide (NO), and anti-inflammatory activity was calculated through the following formula:

Anti-inflammation=(Induced group$_{540\ nm}$−Experimental group$_{540\ nm}$)/(Induced group$_{540\ nm}$−Control group$_{540\ nm}$)

2-2. Results

Anti-inflammatory activity of each test sample is shown in the following Table 2.

TABLE 2

| Apigenin (μM)/ Apigenin (μg/mL) | Inhibition rate | Luteolin (μM)/ Luteolin (μg/mL) | Inhibition rate | Apigenin (μM) + Luteolin (μM) | Inhibition rate |
|---|---|---|---|---|---|
| Batch 1: Mole ratio of apigenin to luteolin = 1:1 or weight ratio of apigenin to luteolin = about 0.94:1 | | | | | |
| 50/13.51 | 0.999 | 50/14.31 | 0.999 | 50 + 50 | 0.999 |
| 25/6.76 | 0.787 | 25/7.16 | 0.841 | 25 + 25 | 0.999 |
| 12.5/3.38 | 0.481 | 12.5/3.58 | 0.563 | 12.5 + 12.5 | 0.910 |
| 6.25/1.69 | 0.263 | 6.25/1.79 | 0.372 | 6.25 + 6.25 | 0.502 |
| 3.125/0.84 | 0.070 | 3.125/0.89 | 0.214 | 3.125 + 3.125 | 0.199 |
| 1.5625/0.42 | 0.011 | 1.5625/0.45 | 0.001 | 1.56 + 1.56 | 0.001 |
| Batch 2: Mole ratio of apigenin to luteolin = 2:1 or weight ratio of apigenin to luteolin = about 1.9:1 | | | | | |
| 50/13.51 | 0.999 | 25/7.16 | 0.757 | 50 + 25 | 0.999 |
| 25/6.76 | 0.741 | 12.5/3.58 | 0.488 | 25 + 12.5 | 0.999 |
| 12.5/3.38 | 0.329 | 6.25/1.79 | 0.299 | 12.5 + 6.25 | 0.541 |
| 6.25/1.69 | 0.237 | 3.125/0.89 | 0.154 | 6.25 + 3.125 | 0.387 |
| 3.125/0.84 | 0.166 | 1.5625/0.45 | 0.058 | 3.125 + 1.5625 | 0.221 |
| 1.5625/0.42 | 0.020 | 0.78/0.22 | 0.001 | 1.56 + 0.78 | 0.127 |

TABLE 2-continued

| Apigenin (μM)/ Apigenin (μg/mL) | Inhibition rate | Luteolin (μM)/ Luteolin (μg/mL) | Inhibition rate | Apigenin (μM) + Luteolin (μM) | Inhibition rate |
|---|---|---|---|---|---|
| Batch 3: Mole ratio of apigenin to luteolin = 5:1 or weight ratio of apigenin to luteolin = about 4.7:1 ||||||
| 50/13.51 | 0.995 | 10/2.86 | 0.803 | 50 + 10 | 0.999 |
| 25/6.76 | 0.938 | 5/1.43 | 0.490 | 25 + 5 | 0.978 |
| 12.5/3.38 | 0.579 | 2.5/0.72 | 0.051 | 12.5 + 2.5 | 0.740 |
| 6.25/1.69 | 0.202 | 1.25/0.36 | 0.001 | 6.25 + 1.25 | 0.445 |
| 3.125/0.84 | 0.009 | 0.625/0.18 | 0.001 | 3.125 + 0.625 | 0.228 |
| 1.5625/0.42 | 0.001 | 0.3125/0.09 | 0.001 | 1.56 + 0.3125 | 0.144 |
| Batch 4: Mole ratio of apigenin to luteolin = 10:1 or weight ratio of apigenin to luteolin = about 9.4:1 ||||||
| 50/13.51 | 0.999 | 5/1.43 | 0.359 | 50 + 5 | 0.999 |
| 25/6.76 | 0.934 | 2.5/0.72 | 0.001 | 25 + 2.5 | 0.957 |
| 12.5/3.38 | 0.454 | 1.25/0.36 | 0.001 | 12.5 + 1.25 | 0.652 |
| 6.25/1.69 | 0.120 | 0.625/0.18 | 0.001 | 6.25 + 0.625 | 0.398 |
| 3.125/0.84 | 0.001 | 0.3125/0.09 | 0.001 | 3.125 + 0.3125 | 0.205 |
| 1.5625/0.42 | 0.001 | 0.15625/0.04 | 0.001 | 1.56 + 0.156 | 0.001 |
| Batch 5: Mole ratio of apigenin to luteolin = 20:1 or weight ratio of apigenin to luteolin = about 18.8:1 ||||||
| 50/13.51 | 0.976 | 2.5/0.72 | 0.161 | 50 + 2.5 | 0.962 |
| 25/6.76 | 0.927 | 1.25/0.36 | 0.005 | 25 + 1.25 | 0.951 |
| 12.5/3.38 | 0.595 | 0.625/0.18 | 0.031 | 12.5 + 0.625 | 0.678 |
| 6.25/1.69 | 0.279 | 0.3125/0.09 | 0.098 | 6.25 + 0.3125 | 0.357 |
| 3.125/0.84 | 0.112 | 0.156/0.04 | 0.001 | 3.125 + 0.15625 | 0.145 |
| 1.5625/0.42 | 0.034 | 0.078/0.02 | 0.001 | 1.56 + 0.078 | 0.038 |
| Batch 6: Mole ratio of apigenin to luteolin = 1:2 or weight ratio of apigenin to luteolin = about 1:2.1 ||||||
| 50/13.51 | 0.999 | 100/28.62 | 0.999 | 50 + 100 | 0.989 |
| 25/6.76 | 0.972 | 50/14.31 | 0.999 | 25 + 50 | 0.999 |
| 12.5/3.38 | 0.594 | 25/7.16 | 0.896 | 12.5 + 25 | 0.990 |
| 6.25/1.69 | 0.289 | 12.5/3.58 | 0.671 | 6.25 + 12.5 | 0.761 |
| 3.125/0.84 | 0.074 | 6.25/1.79 | 0.408 | 3.125 + 6.25 | 0.452 |
| 1.5625/0.42 | 0.189 | 3.125/0.89 | 0.111 | 1.5625 + 3.125 | 0.149 |
| Batch 7: Mole ratio of apigenin to luteolin = 1:5 or weight ratio of apigenin to luteolin = about 1:5.3 ||||||
| 20/5.40 | 0.960 | 100/28.62 | 0.999 | 20 + 100 | 0.988 |
| 10/2.70 | 0.653 | 50/14.31 | 0.999 | 10 + 50 | 0.999 |
| 5/1.35 | 0.300 | 25/7.16 | 0.893 | 5 + 25 | 0.955 |
| 2.5/0.68 | 0.032 | 12.5/3.58 | 0.702 | 2.5 + 12.5 | 0.757 |
| 1.25/0.34 | 0.001 | 6.25/1.79 | 0.439 | 1.25 + 6.25 | 0.484 |
| 0.625/0.17 | 0.001 | 3.125/0.89 | 0.133 | 0.625 + 3.125 | 0.151 |
| Batch 8: Mole ratio of apigenin to luteolin = 1:10 or weight ratio of apigenin to luteolin = about 1:10.6 ||||||
| 10/2.70 | 0.510 | 100/28.62 | 0.999 | 10 + 100 | 0.999 |
| 5/1.35 | 0.206 | 50/14.31 | 0.999 | 5 + 50 | 0.999 |
| 2.5/0.68 | 0.006 | 25/7.16 | 0.904 | 2.5 + 25 | 0.876 |
| 1.25/0.34 | 0.001 | 12.5/3.58 | 0.679 | 1.25 + 12.5 | 0.669 |
| 0.625/0.17 | 0.001 | 6.25/1.79 | 0.344 | 0.625 + 6.25 | 0.325 |
| 0.3125/0.08 | 0.001 | 3.125/0.89 | 0.089 | 0.3125 + 3.125 | 0.013 |
| Batch 9: Mole ratio of apigenin to luteolin = 1:20 or weight ratio of apigenin to luteolin = about 1:21 ||||||
| 2.5/0.68 | 0.149 | 50/14.31 | 0.983 | 2.5 + 50 | 0.974 |
| 1.25/0.34 | 0.065 | 25/7.16 | 0.942 | 1.25 + 25 | 0.925 |
| 0.625/0.17 | 0.065 | 12.5/3.58 | 0.870 | 0.625 + 12.5 | 0.884 |
| 0.3125/0.08 | 0.104 | 6.25/1.79 | 0.670 | 0.3125 + 6.25 | 0.686 |
| 0.156/0.04 | 0.002 | 3.125/0.89 | 0.265 | 0.15625 + 3.125 | 0.270 |
| 0.078/0.02 | 0.020 | 1.5625/0.45 | 0.049 | 0.078 + 1.56 | 0.001 |

Example 3

Evaluation of Synergistic Effects of Apigenin and Luteolin

In this experiment, the synergistic effects of apigenin and luteolin were evaluated by CalcuSyn software (BIOSOFT).

CalcuSyn software is an analysis software which is commonly used to analyze the drug dosage effect of single drug and multiple drugs at present. CalcuSyn software can be used to analyze drug complex interactions and automatically quantify various phenomena such as synergism and inhibition. CalcuSyn software can process the data of individual drugs and combination drugs with constant-ratio or on-constant-ratio, and can evaluate the interaction of combination drugs by the combination index (CI) (Chou and Talalay, *Adv. Enzyme Regul.* 22:27-55 (1984) calculated by CalcuSyn software. Calculation formula for the combination index is shown in the following:

$$\text{Combination index} = C_1/IC_1 + C_2/IC_2$$

$C_1$ and $C_2$ are the respective concentrations of the first compound and the second compound at which the activity of achieving a specific physiological or medical purpose is 50% (or 75%, or 90%) when the first compound and the second compound are analyzed in combination; $IC_1$ and $IC_2$ are the respective concentrations at which the activity of achieving a specific physiological or medical purpose of the first compound and the second compound is 50% (or 75%, or 90%) when the first compound and the second compound are independently analyzed.

Combination index is less than 1, representing that the two compounds have a synergistic effect for specific physiological or medical purposes, combination index is equal to 1, representing that the two compounds have an additive effect for a specific physiological or medical purpose, and combination index is greater than 1, representing that the two compounds have an antagonistic effect on specific physiological or medical purposes (Ting-Chao Chou; Cancer Res; 70(2) Jan. 15, 2010).

3-1. Evaluation of Synergistic Effect of Apigenin and Luteolin on Inhibiting Skin Cell Proliferation

3-1-1. Methods

The experimental results of the 9 batches shown in Table 1 in Example 1 were analyzed by CalcuSyn software to calculate the respective combination indexes of apigenin and luteolin combined in different ratios for inhibiting skin cell proliferation.

3-1-2. Results

The respective combination indexes of apigenin and luteolin combined in different ratios for inhibiting skin cell proliferation calculated by CalcuSyn are shown in the following Table 3.

TABLE 3

| Test sample (Mole ratio in the combination) | | Combination index (CI) | | |
|---|---|---|---|---|
| Apigenin | Luteolin | $IC_{50}$ | $IC_{75}$ | $IC_{90}$ |
| 1 | 1 | 1.56 | 1.56 | 1.57 |
| 2 | 1 | 0.98 | 0.88 | 0.83 |
| 5 | 1 | 0.85 | 0.85 | 0.90 |
| 10 | 1 | 0.90 | 0.93 | 0.95 |
| 20 | 1 | 29.10 | 64.41 | 145.37 |
| 1 | 2 | 1.44 | 1.35 | 1.28 |
| 1 | 5 | 1.17 | 1.10 | 1.06 |
| 1 | 10 | 10.32 | 10.18 | 10.05 |
| 1 | 20 | 30.13 | 35.55 | 41.95 |

According to Table 3, it is known that when the mole ratio of apigenin to luteolin is 2-10:1, apigenin and luteolin have a synergistic effect on inhibiting skin cell proliferation. In contrast, when the mole ratios of apigenin to luteolin are 1:1, 20:1, or 1:2-20, apigenin and luteolin have no synergistic effect on inhibiting skin cell proliferation, and even result in an antagonistic effect.

3-2. Evaluation of Synergistic Effect of Apigenin and Luteolin on Anti-Inflammation

3-2-1. Methods

The experimental results of the 9 batches shown in Table 2 in Example 2 were analyzed by CalcuSyn software to calculate the respective combination indexes of apigenin and luteolin combined in different ratios for anti-inflammation.

3-2-2. Results

The respective combination indexes of apigenin and luteolin combined in different ratios for anti-inflammation calculated by CalcuSyn are shown in the following Table 4.

TABLE 4

| Test sample (Mole ratio in the combination) | | Combination index (CI) | | |
|---|---|---|---|---|
| Apigenin | Luteolin | $IC_{50}$ | $IC_{75}$ | $IC_{90}$ |
| 1 | 1 | 1.61 | 1.49 | 1.37 |
| 2 | 1 | 0.70 | 0.60 | 0.52 |
| 5 | 1 | 0.54 | 0.75 | 0.77 |
| 10 | 1 | 0.72 | 0.75 | 0.77 |
| 20 | 1 | 0.94 | 0.96 | 0.98 |
| 1 | 2 | 1.58 | 1.52 | 1.47 |
| 1 | 5 | 1.22 | 1.31 | 1.44 |
| 1 | 10 | 1.10 | 1.14 | 1.18 |
| 1 | 20 | 1.51 | 1.30 | 1.12 |

According to Table 4, it is known that when the mole ratio of apigenin to luteolin is 2-20:1, apigenin and luteolin have a synergistic effect on anti-inflammation. In contrast, when the mole ratio of apigenin to luteolin is 1:1 or 1:2-20, apigenin and luteolin have no synergistic effect on anti-inflammation, and even result in an antagonistic effect.

3-3. Conclusion

Based on the foregoing results, it is clear that, in terms of inhibiting skin cell proliferation and anti-inflammation, not all combinations of apigenin and luteolin in any ratio can have a synergistic effect, but apigenin and luteolin have to be in specific combination ratio for them to work synergistically. Furthermore, when the mole ratio of apigenin to luteolin is about 2-20:1, apigenin and luteolin can have synergistic effects on inhibiting skin cell proliferation and/or anti-inflammation.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A skin cell proliferation inhibition and/or anti-inflammation pharmaceutical or health care composition, comprising:
    a combination of apigenin and luteolin as an active ingredient,
    wherein the weight ratio of the apigenin to the luteolin is about 1.5-25:1 or the mole ratio of the apigenin to the luteolin is about 1.5-25:1, and the apigenin and the luteolin have a synergistic effect on anti-inflammation, or
    wherein the weight ratio of the apigenin to the luteolin is about 1.5-15:1 or the mole ratio of the apigenin to the luteolin is about 1.5-15:1, and the apigenin and the luteolin have a synergistic effect on skin cell proliferation inhibition and/or anti-inflammation.

2. The skin cell proliferation inhibition and/or anti-inflammation pharmaceutical or health care composition as claimed in claim 1, wherein the skin cell comprises a keratinocyte or a skin fibroblast.

3. The skin cell proliferation inhibition and/or anti-inflammation pharmaceutical or health care composition as claimed in claim 1, wherein the inflammation comprises an inflammatory response involving macrophages.

4. The skin cell proliferation inhibition and/or anti-inflammation pharmaceutical or health care composition as claimed in claim 1, further comprising a pharmaceutically acceptable vehicle, carrier or salt.

5. The skin cell proliferation inhibition and/or anti-inflammation pharmaceutical or health care composition as claimed in claim 4, wherein a total content of the apigenin and the luteolin is about 0.1-20 wt %.

6. The skin cell proliferation inhibition and/or anti-inflammation pharmaceutical or health care composition as claimed in claim 1, wherein the skin cell proliferation inhibition and/or anti-inflammation pharmaceutical or health care composition is the skin cell proliferation inhibition and/or anti-inflammation pharmaceutical composition.

7. The skin cell proliferation inhibition and/or anti-inflammation pharmaceutical or health care composition as claimed in claim 6, wherein the skin cell proliferation inhibition and/or anti-inflammation pharmaceutical composition is a topical dosage form, wherein the topical dosage form comprises an ointment, a cream, a solution or a gel.

8. The skin cell proliferation inhibition and/or anti-inflammation pharmaceutical or health care composition as claimed in claim 7, wherein the skin cell proliferation inhibition and/or anti-inflammation pharmaceutical composition is a skin disease treatment pharmaceutical composition.

9. The skin cell proliferation inhibition and/or anti-inflammation pharmaceutical or health care composition as claimed in claim 8, wherein the skin disease treatment pharmaceutical composition is a psoriasis treatment pharmaceutical composition or an allergic or contact dermatitis treatment pharmaceutical composition.

\* \* \* \* \*